| United States Patent [19] | [11] Patent Number: 4,476,326 |
| Lin et al. | [45] Date of Patent: Oct. 9, 1984 |

[54] PROCESS FOR THE SYNTHESIS OF ETHANOL AND ACETALDEHYDE USING COBALT COMPOUNDS WITH NOVEL PROMOTERS

[75] Inventors: Jiang-Jen Lin, Williamson; John F. Knifton, Austin, both of Tex.

[73] Assignee: Texaco Inc., White Plains, N.Y.

[21] Appl. No.: 463,380

[22] Filed: Feb. 3, 1983

[51] Int. Cl.³ .............................................. C07C 45/49
[52] U.S. Cl. .................................... 568/487; 568/454; 568/490; 568/909
[58] Field of Search ................. 568/454, 487, 490, 909

[56] References Cited

U.S. PATENT DOCUMENTS

| 3,285,948 | 11/1966 | Butter | 568/487 |
| 4,239,924 | 12/1980 | Pretzer et al. | 568/487 |
| 4,239,925 | 12/1980 | Pretzer et al. | 568/487 |
| 4,361,706 | 11/1982 | Habib | 568/487 |

FOREIGN PATENT DOCUMENTS 2082181  3/1982  United Kingdom ................ 568/487

*Primary Examiner*—Werren B. Lone
*Attorney, Agent, or Firm*—Robert A. Kulason; Jack H. Park; Cynthia L. Kendrick

[57] ABSTRACT

Ethanol and/or acetaldehyde are prepared in good yield by contacting methanol, hydrogen and carbon monoxide with a catalyst system comprising a cobalt-containing compound and a promoter in the presence of an inert oxygenated solvent at a temperature of from about 50° C. to about 350° C. and a pressure of at least 500 psig or greater. The combination of cobalt-containing compound and promoter may be (a) a cobalt-containing compound with an organo-sulphur compound, (b) an iodide-containing cobalt compound with a nitrogen-containing compound as promoter, and (c) a cobalt-containing compound with 1,1'-bis(diphenylphosphino)ferrocene.

14 Claims, No Drawings

PROCESS FOR THE SYNTHESIS OF ETHANOL AND ACETALDEHYDE USING COBALT COMPOUNDS WITH NOVEL PROMOTERS

FIELD OF THE INVENTION

This invention relates to a process for the preparation of ethanol and acetaldehyde by the reaction of synthesis gas, i.e. a mixture of hydrogen and carbon monoxide, with methanol, optionally in the presence of an oxygenated solvent, using as a catalyst a cobalt-containing compound and novel promoters.

PRIOR ART

There is a commercial potential for the use of ethanol as a gasoline extender. A large number of processes have been described in the art for reacting methanol with carbon monoxide and hydrogen in the presence of catalyst systems to produce ethanol. A general disadvantage of the art described processes is that they all produce a wide variety of other related products such as higher molecular weight alcohols, aldehydes, ketones, carboxylic acids, esters, etc.

Earliest research on carbon monoxide/hydrogen chemistry dates back to 1902 when Sabatier and Senderens passed CO and $H_2$ (1:3) over reduced nickel at 1 atm and produced methane. It was reported by BASF in 1913 that at higher pressures (100–200 atm) and temperatures (300°–400° C.) the major products are liquids. Later in 1923 Fischer and Tropsch disclosed the use of alkalized iron turnings as catalysts for the production of an oily liquid from CO and $H_2$ at 100–150 atm and 400°–425° C. This product contained mainly oxygenated compounds such as alcohols, acids, aldehydes, ketones and esters, and a very small quantity of hydrocarbons.

Continuing research with Fischer-Tropsch catalysts has lead to the development of commercial scale plants for methanol synthesis from carbon monoxide and hydrogen.

In 1949 Wender et al. (J.A.C.S., 71,4160) reported the homologation of alcohols by reaction with synthesis gas in the presence of a cobalt catalysts under oxo reaction conditions. There is described the conversion of t-butyl alcohol into isoamyl alcohol, and the conversion of benzyl alcohol into β-phenylethyl alcohol. In 1951 these workers reported the conversion of methanol into ethanol under oxo reaction conditions with a cobalt catalysts. Other products of the reaction included methyl formate, methyl acetate, ethyl acetate, acetaldehyde, propyl alcohol, butyl alcohol and methane.

U.S. Pat. No. 2,623,906, entitled PREPARATION OF ORGANIC HYDROXY-CONTAINING COMPOUNDS BY REACTING ALCOHOLS WITH CARBON MONOXIDE AND HYDROGEN, issued to Gresham on Dec. 30, 1952, relates to a procedure for synthesizing mono and polyfunctional oxygen-containing organic compounds by the reaction of alcohols, carbon monoxide and hydrogen. Catalysts described as suitable for use include various cobalt compounds, for example, cobalt carbonyl, cobalt carbonyl hydride, metallic cobalt, and organic and inorganic cobalt salts. The process, however, suffers from the disadvantage of poor product distribution.

Another process is set forth in U.S. Pat. No. 3,248,432, entitled PROCESS FOR THE PRODUCTION OF ETHYL ALCOHOL, issued to Riley et al. on Apr. 26, 1966, which relates to a process for the production of ethyl alcohol by the interaction of methanol, carbon monoxide and hydrogen at elevated temperature and pressure in the presence of a cobalt catalyst and an iodine promoter. Examples of suitable cobalt sources are described as any water-soluble source of cobalt, for example, the lower salts of alkanoate cobalt, such as cobalt acetate, cobalt formate, cobalt propionate, and the like.

U.S. Pat. No. 3,285,948 discloses basically the same idea as U.S. Pat. No. 3,248,432, but the cobalt catalyst is promoted with iodine and a metal halide selected from ruthenium halide and osmium halide.

British Pat. Specification No. 1,546,428 entitled PRODUCTION OF ETHANOL FROM METHANOL CARBON MONOXIDE AND HYDROGEN, filed by Shell International Research on June 8, 1976, relates to a process for producing alcohols which utilizes any soluble cobalt source which can generate a cobalt carbonyl or hydrocarbonyl by reaction with the synthesis gas. For example, sources of cobalt suitable for use are cobalt iodide or cobalt metal from which ions can be generated in situ. Organic salts of cobalt such as cobalt acetate, formate, or propionate are described as especially good sources and an iodide or bromide promoter is also utilized. In addition, the use of a tertiary phosphine is described as affording improved selectivity to the formation of alcohols.

U.S. Pat. No. 4,133,966 discloses a four component catalyst system composed of cobalt acetylacetonate, a tertiary organo Group VA compound, an iodine promoter, and, as a second promoter, a ruthenium compound.

U.S. Pat. No. 4,111,837 discloses a heterogeneous co-catalyst for the homologation of alkanol with hydrogen and carbon monoxide which consists of an alkanol solution of cobalt carbonyl in contact with surface-active rhenium metal.

U.S. Pat. No. 4,618,391 teaches that an improvement in the process wherein carbon monoxide and hydrogen are reacted in the liquid phase in the presence of a cobalt carbonyl catalyst by which increased amounts of ethanol may be produced is to conduct the reaction in the presence of a non-polar, substantially inert, oxygenated hydrocarbon solvent.

U.S. Pat. No. 4,233,466 discloses a process for producing ethanol from the reaction of methanol, hydrogen and carbon monoxide catalyzed by a phosphine plus iodine promoted cobalt-ruthenium catalyst wherein the improvement consists of maintaining the phosphine to halide concentration ratio within a critical range.

In U.S. Pat. No. 4,239,924 what is claimed is a process for selectively producing ethanol which comprises introducing into a reaction zone methanol, hydrogen, carbon monoxide, a cobalt-tricarbonyl complex, an iodide promoter and a ruthenium compound, and then subjecting the contents of said reaction zone to an elevated temperature and pressure for a time sufficient to convert methanol to ethanol. U.S. Pat. No. 4,239,925 is similar, but includes only an iodine promoter.

U.S. Pat. No. 4,201,868 discloses a catalyst system comprising a cobalt carbonyl in complex combination with an organic nitrogen ligand, which affects the reacting of methanol with carbon monoxide and hydrogen to produce increased amounts of methyl acetate, acetaldehyde and dimethyl acetal. The catalyst system is free of halide moiety and the product selectivity to ethanol is minimal.

It is an object of this invention to provide a catalyst system with novel promoters for the homologation of methanol. Another object is to provide a catalyst system adapted for high efficiency conversion of methanol and high selectivity for ethanol and, under some conditions, acetaldehyde. It is a further object of this invention to maintain the improved results of the novel promoters of this catalyst system when it is used under conditions where the use of a iodine is undesirable. In other words the system may be used in the presence or absence of iodine.

An additional advantage is evidenced by increased recovery of cobalt from the system in many examples.

Other objects and advantages of this invention shall become apparent from the following description and exemplary data.

SUMMARY OF THE INVENTION

One or more objects of the present invention are accomplished by the provision of an improved homologation process for producing ethanol and acetaldehyde which comprises reacting methanol with carbon monoxide and hydrogen in the presence of a catalyst system comprising a cobalt-containing compound and a promoter. Said promoter may be selected from the group consisting of: (a) a compound containing one or more tertiary phosphorous or nitrogen donor atoms, and (b) an organo-sulphur compound containing one or more sulphur atoms in the +2 or +4 oxidation state, as well as mixtures thereof. Optionally said homologation process is conducted in the presence of an oxygenated solvent, heating the resultant reaction mixture to a temperature of from about 50° C. to about 350° C. and at a pressure of about 500 psig or greater.

Recovery of ethanol and acetaldehyde from the reaction product can be carried out in any conventional or convenient manner such as by distillation or extraction.

The high selectivity to ethanol achieved in this process ranges up to a value of 60% while conversions of methanol reach the very high figure of 98%. When reaction conditions are varied, acetaldehyde can be produced selectively in ranges up to 61%.

DETAILED DESCRIPTION OF THE INVENTION

This invention relates to a process for preparing ethanol and acetaldehyde which comprises reacting a mixture of hydrogen, carbon monoxide and methanol in the presence of a catalyst system comprising a cobalt-containing compound and a promoter selected from the group consisting of (a) a compound containing one or more phosphorus or nitrogen donor atoms or (b) an organo-sulphur compound containing one or more sulphur atoms in the +2 or +4 oxidation state, as well as mixtures thereof, optionally in the presence of a substantially inert solvent, heating said reaction mixture to a temperature of from about 50° C. to about 350° C. and at a pressure of from about 500 psig to 5000 psig.

Catalysts that are suitable for use in the practice of this invention contain cobalt. The cobalt-containing compounds may be chosen from a wide variety of organic or inorganic compounds, complexes, etc., as will be shown and illustrated below. It is only necessary that the catalyst precursor actually employed contain said cobalt in any of its ionic states. The actual catalytically active species is then believed to comprise cobalt in complex combination with one or more promoters and with carbon monoxide and hydrogen. The most effective catalyst is achieved where the cobalt and the promoter species are solublized in the methanol coreactant and the oxygenated hydrocarbon solvent.

The cobalt-containing catalyst precursors may take many different forms. For instance, the cobalt may be added to the reaction mixture in an oxide form, as in the case of, for example, cobalt(II) oxide (CoO) or cobalt-(II, III) oxide ($Co_3O_4$). Alternatively, it may be added as the salt of a mineral acid, as in the case of cobalt(II) chloride ($CoCl_2$), cobalt(II) chloride hydrate ($CoCl_2.6H_2O$), cobalt(II) bromide ($CoBr_2$), cobalt(II) iodide ($CoI_2$) and cobalt(II) nitrate hydrate ($Co(NO_3)_2.6H_2O$), etc., or as the salt of a suitable organic carboxylic acid, for example, cobalt(II) formate, cobalt(II) acetate, cobalt(II) propionate, cobalt naphthenate, as well as in complexes such as cobalt acetylacetonate, etc. The cobalt may be added to the reaction zone as a carbonyl or hydrocarbonyl derivative. Here, suitable examples include dicobalt octacarbonyl ($Co_2(CO)_8$), cobalt hydrocarbonyl ($HCo(CO)_4$) and substituted carbonyl species such as the triphenylphosphine cobalt tricarbonyl dimer, etc.

Preferred cobalt-containing compounds include oxides of cobalt, cobalt salts of a mineral acid, cobalt salts of organic carboxylic acids and cobalt carbonyl or hydrocarbonyl derivatives. Among these, particularly preferred are cobalt(II) chloride, cobalt(III) acetylacetonate, cobalt(II) acetate, cobalt(II) propionate, and especially preferred are dicobalt octacarbonyl and cobalt iodide.

The iodide-containing cobalt compounds are defined to be different forms of cobalt iodide such as cobalt(II) iodide, cobalt(II) iodide, hydrate or the combination of a iodide-free cobalt species plus a organic iodide.

The novel promoters suitable for use in conjunction with a cobalt-containing compound in the desired homologation reaction may take many different forms.

Generally these promoters contain one or more nitrogen, phosphorous, or sulfur atoms per molecule, each bonded to one or more carbon atoms.

Suitable nitrogen-containing promoters contain one or more tertiary nitrogen donor atoms bonded to one or more carbon atoms. Said class of promoters include N-heterocyclics such as pyridine, 2-hydroxypyridine, 2-vinylpyridine, 2,4-dihydroxypyridine, and 8-hydroxyquinoline, as well as aliphatic amines such as N,N,N',N'-tetramethylpropylenediamine and N,N,N',N'-tetramethylethylenediamine (TMEDA), and aliphatic nitriles such as succinonitrile and acrylonitrile.

Most preferred is 8-hydroxyquinoline.

Suitable phosphorus-containing promoters contain one or more tertiary phosphorus donor atoms bonded to one or more carbon atoms. Said class of promoters include phosphines, such as triphenylphosphine, bis(1,4-diphenylphosphino)butane, 1,1' bis(diphenylphosphino)ferrocene, tributylphosphine, tri-p-tolylphosphine, bis(1,2-diphenylphosphino)ethane, tricyclohexylphosphine, and tris(2-diphenylphosphinoethyl)phosphine. The most preferred phosphine promoter for the process of this invention is 1,1'-bis(diphenylphosphino)ferrocene.

Compounds containing one or more sulphur atoms bonded to one or more carbon atoms are also useful promoters in the process of this invention. Such organo-sulphur compounds include, but are not limited to, phenyl sulphide, diphenyl sulphoxide, dimethylsulphoxide, dibutylsulphide, cis-bis(1,2-benzylthio)ethane, and 1,2-dimercapto-4-methylbenzene.

The solvent useful in the process of this invention is an oxygenated hydrocarbon i.e., a compound composed only of carbon, hydrogen and oxygen and one in which the only oxygen atoms present are in ether groups, ester groups, ketone carbonyl groups or hydroxyl groups of alcohols. Generally, the oxygenated hydrocarbon will contain 3 to 12 carbon atoms and preferably a maximum of 3 oxygen atoms. The solvent must be substantially inert under reaction conditions, it must be relatively non-polar and it must be one which has a normal boiling point of at least 65° C. at atmospheric pressure and preferably, the solvent will have a boiling point greater than that of ethanol and other oxygen-containing reaction products so that recovery of the solvent by distillation is facilitated.

Preferred ester type solvents are the aliphatic and acrylic carboxylic acid monoesters as exemplified by butyl acetate, methyl benzoate, isopropyl iso-butyrate, and propyl propionate as well as dimethyl adipate. Useful alcohol-type solvents include monohydric alcohols such as cyclohexanol, 1-hexanol, 2-hexanol, neopentanol, 2-octanol, etc. Suitable ketone-type solvents include, for example, cyclic ketones such as cyclohexanone, 2-methylcyclohexanone, as well as acyclic ketones such as 2-pentanone, butanone, acetophenone, etc. Ethers which may be utilized as solvents include cyclic, acyclic and heterocyclic materials. Preferred ethers are the heterocyclic ethers as illustrated by 1,4-dioxane and 1,3-dioxane. Other suitable ether solvents include isopropyl propyl ether, diethylene glycol dibutyl ether, dibutyl ether, ethyl butyl ether, diphenyl ether, heptyl phenyl ether, anisole, tetrahydrofuran, etc. alkanols such as methanol and acid esters such as methyl acetate.

The most preferred solvents and those which seem to most noticeably effect an increase in ethanol selectivity are p-dioxane or methyl isobutyl ketone (MIBK).

The cobalt and nitrogen-, phosphorous- and sulfur-containing promoter catalyst system is present in a catalytically effective amount, sufficient to catalyze the reaction, preferably from $1 \times 10^{-6}$ to 50 weight percent, most preferably from $1 \times 10^{-3}$ to 10 weight percent, based on the amount of methanol present.

The quantity of cobalt catalyst employed in the instant invention is not critical and may vary over a wide range. In general, this improved process is desirably conducted in the presence of a catalytically effective quantity of the active cobalt species, in conjunction with one or more nitrogen, phosphorous or sulphur-containing promoters which give the desired products in reasonable yields. The reaction proceeds when employing as little as about $1 \times 10^{-6}$ weight percent, and even lesser amounts, of cobalt together with about $1 \times 10^{-6}$, weight percent of a promoter, basis the total weight of the reaction mixture. The upper concentration is dictated by a variety of factors including catalyst cost, partial pressures of carbon monoxide and hydrogen, operating temperature etc. A cobalt catalyst concentration of from about $1 \times 10^{-5}$ to about 30 weight percent cobalt in conjunction with an amine, phosphine, or sulfur promoter concentration of from about $1 \times 10^{-5}$ to about 30 weight percent based on the total weight of reaction mixture is generally desirable in the practice of this invention.

The mole ratio of cobalt to promoter can be from 0.01 to 100, preferably from 0.1 to 10.

The relative amounts of carbon monoxide and hydrogen which may be initially present in the syngas mixture are also variable, and these amounts may be varied over a wide range. In general, the mole ratio of $CO:H_2$ is in the range from 20:1 up to about 1:20, preferably from about 5:1 to 1:5, although ratios outside these ranges may also be employed. Particularly in continuous operations, but also in batch experiments, the carbon monoxide-hydrogen gaseous mixtures may also be used in conjunction with up to 50% by volume of one or more inert gases such as nitrogen, argon, neon and the like, or they may include gases that may, or may not, undergo reaction under CO hydrogenation conditions such as carbon dioxide, hydrocarbons such as methane, ethane, propane and the like, ethers such as dimethyl ether, methylethyl ether and diethyl ether.

The temperature range which can usefully be employed in these synthesis is a further variable, dependent upon other experimental factors, including the pressure, and the concentration and choice of particular species of the cobalt-containing compound and promoter, among other things. The range of operability is from about 50° to about 350° C. when superatmospheric pressures of syngas are employed. A narrower range of about 100° to about 250° C. represents the preferred temperature range.

Superatmospheric pressure of about 500 psi or greater leads to substantial yields of desirable ethanol by the process of this invention. A preferred operating range is from about 1000 psi to about 10,000 psi although pressures above 10,000 psi also provide useful yields of the desired products. The pressures referred to here represent the total pressure generated by all the reactants, although they are substantially due to the carbon monoxide and hydrogen fractions in these examples.

As far as can be determined, without limiting the invention thereby, the one-step process herein utilizing the disclosed catalysts leads primarily to the formation of ethanol and acetaldehyde. By-products such as water, n-propanol, methyl acetate, ethyl acetate and acetic acid are also detected in the liquid products fraction.

The novel process of this invention can be conducted in a batch, semicontinuous or continuous fashion. The catalyst may be initially introduced into the reaction zone batchwise, or it may be continuously or intermittently introduced into such a zone during the course of the synthesis reaction. Operating conditions can be adjusted to optimize the formation of the desired alcohol products, and said material may be recovered by methods well known in the art, such as distillation, fractionation, extraction and the like. A fraction rich in the cobalt-containing compound and the promoter compound may then be recycled to the reaction zone, if desired, and additional products generated.

The products formed by the process of this invention have been identified in this work by one or more of the following analytical procedures, viz, gas-liquid phase chromatograph (glc), infrared (ir), mass spectrometry, nuclear magnetic resonance (nmr) and elemental analysis, or a combination of these techniques. Analysis have, for the most part, been by parts per weight; all temperatures are in degrees centigrade and all pressures in pounds per square inch gauge (psig).

To illustrate the process of the invention, the following examples are given. It is understood, however, that the examples are given in the way of illustration and are not to be regarded as limiting the invention in any way.

EXAMPLE I

TABLE I

| | | Ethanol Synthesis by $Co_2(CO)_8$ + Phosphine Promoter* | | | | | | | |
|---|---|---|---|---|---|---|---|---|---|
| | | Methanol conversion | ← Product selectivities (wt %) → | | | | | | Cobalt** recovery (%) |
| Example | Promoter(mmole used) | % | ethanol | n-propanol | acetaldehyde | methyl acetate | ethyl acetate | Water (%) | Wt. gain (g) | |
| I | 1,1'-Bis(diphenylphosphino)ferrocene (0.25) | 82 | 58 | 14 | 7 | 5 | 2 | 11.4 | 3.9 | 96 |
| II | 1,1'-Bis(diphenylphosphino)ferrocene (1.0) | 74 | 54 | 11 | 9 | 0 | 0 | 9.6 | 3.3 | — |
| III | $Ph_3P$ (0.25) | 81 | 55 | 15 | 6 | 5 | 2 | 11.5 | 4.4 | 87 |
| IV | Bis(1,4-diphenylphosphino)butane (0.25) | 44 | 39 | 11 | 14 | 4 | 7 | 5.8 | 0.7 | 27 |
| V Comparative | None | 78 | 67 | 9 | 4 | 4 | 1 | 10.8 | 2.3 | 2 |

*$Co_2(CO)_8$ (0.34g, 1.0 mmole) and methanol (5.5g) were used.
Reaction conditions: $Co/H_2$ = 1:2 4000 psi 180° C. and 18 hr.
Solvent: P.dioxane (14.0g)
**Cobalt recovery in solution, estimated by atomic absorption analysis of crude liquid product.

This example demonstrates high methanol conversion and high selectivity for ethanol using dicobalt octacarbonyl and 1,1'-bis(diphenylphosphino) ferrocene as a promoter. In this example a glass liner was charged with dicobalt octacarbonyl (0.34 g, 1 mm) 1,1'-bis(diphenylphosphino)ferrocene (0.14 g, 0.25 mm), methanol (5.5 g) and p-dioxane (14.0 g). The glass liner was placed in a stainless steel reactor. The reactor was purged of air and pressured to 1000 psi with a mixture of CO and $H_2$ (1:2 molar ratio), then was heated to 180° C., while it was agitated by rocking. The pressure was brought up to 4000 psi and maintained by addition of syngas through a large surge tank. After a 16 hour reaction period, the reactor was allowed to cool to room temperature. An off-gas sample was taken and excess gas vented from the reactor, following which 23.9 g brown liquid was recovered.

The product liquid was analyzed by glc. The carbon selectivities to ethanol, acetaldehyde, n-propanol, methyl acetate and ethyl acetate (basis methanol converted) were then estimated to be as follows:
58% ethanol,
7% acetaldehyde,
14% n-propanol,
5% methyl acetate,
2% ethyl acetate.

The methanol conversion was calculated to be 82%. The water content was determined by Karl Fischer titration, as 11.4%. A typical off-gas analysis showed:
51.4% hydrogen,
41.0% carbon monoxide,
2.1% methane,
2.9% carbon dioxide.

The cobalt elemental analysis via atomic absorption has shown 4605 ppm cobalt in the crude product solution, which was calculated as 96% cobalt recovery.

In Examples II–IV, the procedure of Example I was followed. However, different phosphorous-containing promoters, including triphenylphosphine and bis(1,4-diphenylphosphino)butane, were used and the molar ratio of cobalt-containing compound to promoter was varied. Example V is a comparative example where no phosphorous-containing promoter was added. Results are summarized in Table I which follows.

It may be noted that in these examples cobalt recovery in solution is considerably improved in the presence of triphenylphosphine and bis(1,4-diphenylphosphino)butane compared with the control Example V, with no added promoter.

EXAMPLE VI

This example demonstrates the use of cobalt(II) iodide and a particular phosphine promoter in the homologation of methanol to ethanol. In this example a glass liner was charged with cobalt(II) iodide (0.34 g, 1 mmole), 1,1'-bis(diphenylphosphino)ferrocene (0.243 g, 0.50 mmole), methanol (5.5 g) and p-dioxane (20.0 g). The glass liner was placed in a stainless steel reactor. The reactor was purged of air and pressured to 500 psi with a mixture of CO and $H_2$ (1:2 molar ratio), then was heated to 180° C., while it was agitated by rocking. The pressure was brought up to 2000 psi and maintained at this pressure by addition of syngas through a surge tank. After 18 hours reaction period, the reactor was allowed to cool to room temperature. An off-gas sample was taken and excess gas vented from the reactor following which 28.4 g of a brown solution was obtained.

The product liquid was analyzed by glc. The product selectivities (based on methanol converted) were then estimated to be as follows:
60% ethanol,
2% n-propanol,
18% acetaldehyde,
2% methyl acetate,
4% ethyl acetate.

The methanol conversion was calculated to be 70%. The water content was determined by Karl-Fischer titration, as 7.54%. A typical off-gas sample showed the presence of:
35.5% carbon monoxide,
56.3% hydrogen,
1.5% methane,
3.6% carbon dioxide.

The cobalt elemental analysis via atomic absorption showed 1724 ppm in the crude product solution, which was calculated as 82% cobalt recovery.

The procedure of Example VI was used in Examples VII to X (Table II) where the effect on methanol homologation to ethanol using cobalt(II) iodide with different phosphine promoters, different cobalt-to-phosphorous mole ratios and different syngas pressures was demonstrated.

It may be noted that in this Table, the cobalt catalyst system with 1,1'-bis(diphenylphosphino)ferrocene as promoter provides the highest selectivity to desired ethanol product.

TABLE II

Ethanol Synthesis by CoI$_2$ + Phosphine Promoters*[1]

| Example | Promoter (mmole used) | Syngas pressure (psi) | Methanol conversion (%) | ethanol | n-propanol | acetaldehyde | methyl acetate | ethyl acetate | Water (%) | Wt. gain (g) | cobalt recovery (%) |
|---|---|---|---|---|---|---|---|---|---|---|---|
| VI | 1,1'-Bis(diphenylphosphino)ferrocene (0.5)[2] | 2000 | 70 | 60 | 2 | 18 | 2 | 4 | 7.5 | 2.3 | 82 |
| VII | 1,1'-Bis(diphenylphosphino)ferrocene (0.5)[2] | 1000 | 32 | 39 | 0 | 23 | 2 | 34 | 3.1 | 0 | 88 |
| VIII | Ph$_3$P (1)[3] | 2000 | 80 | 35 | 0 | 21 | 4 | 10 | 12.5 | 3.1 | 94 |
| IX | Bis(1,4-diphenylphosphino)butane (0.25)[3] | 2000 | 88 | 28 | 0 | 26 | — | 12 | 12.9 | 2.7 | 87 |
| X (Comparative) | None[3] | 2000 | 92 | 29 | 3 | 29 | 0 | 8 | 15.3 | 3.4 | 76 |

[1] reaction conditions: CO/H$_2$ = 1:2, 180° C. and 18 hr.
[2] CoI$_2$: 1 mmole; p-dioxane 20g
[3] CoI$_2$: 2 mmole; p-dioxane 14g

EXAMPLES XI–XVI

In these examples the procedures of Examples I and VI were used, both cobalt(II) iodide and dicobalt octacarbonyl were used in combination with different sulphur-containing promoters, including diphenylsulphoxide and diphenylsulphide. Results are summarized in Table III.

It may be noted that:

(a) in Examples XI and XII, using cobalt octacarbonyl coupled with diphenylsulphoxide and diphenylsulphide, cobalt recovery in solution is superior to control experiment V.

(b) In Examples XIII to XVI, using cobalt(II) iodide and diphenylsulphoxide, acetaldehyde selectivity and cobalt recovery are superior to the comparative Example X with cobalt(II) iodide and no added promoter.

EXAMPLES XVII–XXIV

These examples demonstrate the effect of using nitrogen-containing promoters, such as 8-hydroxyquinoline, 2-hyroxypyridine, succinonitrile and tetramethylethylenediamine promoters, in combination with an iodide-containing cobalt catalyst such as cobalt(II) iodide. The product selectivity to acetaldehyde and ethanol and the methanol conversion are affected by various promoters, syngas pressure and reaction temperature. It is noted 61% acetaldehyde was obtained in Example XVII using CoI$_2$-8-hydroxyquinoline at 3000 psig and 140° C. and 52% acetaldehyde selectivity was achieved by Example XXIII using CoI$_2$-TMEDA catalyst. Cobalt recovery in solution at the end of each of these homologation syntheses is superior in these examples (range 81–100%) compared to the comparative Example X. Ethanol selectivity (55%) in Example XXIV using cobalt(II) iodide plus TMEDA is superior to the comparative Example X with cobalt(II) iodide and no added promoter.

TABLE III

Ethanol and Acetaldehyde Synthesis by Cobalt Catalyst + Organo-Sulphur Promoters

| Example | Catalyst | promoter (mmole used) | Syngas pressure (psi) | temperature (°C.) | methanol conversion (%) | ethanol | n-propanol | acetaldehyde | methyl acetate | ethyl acetate | Water (%) | Wt. gain | cobalt recovery (%) |
|---|---|---|---|---|---|---|---|---|---|---|---|---|---|
| XI | Co$_2$(CO)$_8$ | Ph$_2$SO (0.25) | 3950 | 180 | 84 | 53 | 12 | 5 | 4 | 1 | 12.0 | 3.8 | 79 |
| XII | Co$_2$(CO)$_8$ | Ph$_2$S (0.25) | 4000 | 180 | 88 | 53 | 11 | 6 | 4 | 1 | 10.5 | 2.2 | 92 |
| XIII | CoI$_2$ | Ph$_2$SO (0.25) | 4000 | 180 | 98 | 17 | 0 | 32 | 1 | 2 | 17.4 | 4.8 | 83 |
| XIV | CoI$_2$ | Ph$_2$SO (2.0) | 3000 | 140 | 84 | 8 | 4 | 57 | 4 | 11 | 12.1 | 2.5 | 100 |
| XV | CoI$_2$ | Ph$_2$SO (2.0) | 3000 | 120 | 78 | 2 | 0 | 47 | 13 | 22 | 9.4 | 0.4 | 90 |
| XVI | CoI$_2$ | Ph$_2$SO (0.25) | 2000 | 180 | 86 | 28 | 0 | 41 | 2 | 0 | 9.6 | 1.3 | 100 |

Catalyst: Co$_2$(CO)$_8$ (1 mmole) or CoI$_2$ (2.0 mmoles) was used.
Condition: Co/H$_2$ = 1:2 180° C. Methanol (5.5g) and p-dioxane (14.0g) were used.

TABLE IV

Ethanol and Acetaldehyde Synthesis by CoI$_2$ and Nitrogen-Containing Promoters

| Example | promoter (mmole used) | Syngas pressure (psi) | temperature (°C.) | methanol conversion (%) | ethanol | n-propanol | acetaldehyde | methyl acetate | ethyl acetate | Water (%) | Wt. gain (g) | cobalt recovery (%) |
|---|---|---|---|---|---|---|---|---|---|---|---|---|
| XVII | 8-hydroxyquinoline[b] (2) | 3000 | 140 | 87 | 6 | 0 | 61 | 7 | 9 | 14.4 | 2.8 | 88 |
| XVIII | 8-hydroxyquinoline[b] | 3000 | 120 | 74 | 2 | 2 | 55 | 13 | 15 | 9.5 | 1.0 | 85 |

TABLE IV-continued

Ethanol and Acetaldehyde Synthesis by CoI₂ and Nitrogen-Containing Promoters

| Example | promoter (mmole used) | Syngas pressure (psi) | temperature (°C.) | methanol conversion (%) | ethanol | n-propanol | acetaldehyde | methyl acetate | ethyl acetate | Water (%) | Wt. gain (g) | cobalt recovery (%) |
|---|---|---|---|---|---|---|---|---|---|---|---|---|
| XIX | 8-hydroxyquinoline[b] (2) | 2000 | 180 | 37 | 0 | 0 | 34 | 8 | 23 | 6.9 | 0 | 100 |
| XX | 2-hydroxypyridine[a] (1) | 1450 | 180 | 39 | 6 | 0 | 26 | 4 | 56 | 4.4 | 0 | 100 |
| XXI | 2-hydroxypyridine[a] (1) | 2000 | 180 | 74 | 29 | 0 | 20 | 4 | 2 | 14.0 | 2.6 | 95 |
| XXII | Succinonitrile[a] (0.25) | 1500 | 180 | 72 | 36 | 0 | 23 | 4 | 27 | 8.8 | 1.2 | 81 |
| XXIII | TMEDA[b] (0.5) | 3000 | 140 | 81 | 10 | 0 | 52 | 6 | 9 | 10.9 | 3.2 | 89 |
| XXIV | TMEDA[b] (1.0) | 2000 | 180 | 86 | 55 | 11 | 15 | 3 | 6 | 12.0 | 3.5 | 90 |

Note:
[a] CoI₂: 1 mmole
[b] CoI₂: 2 mmole
[c] CO/H₂ = 1:2 16–18 hrs methanol (5.5g) and p-dioxane (14.0g) were used.

What is claimed is:

1. A process for preparing ethanol and acetaldehyde which comprises reacting a mixture of hydrogen, carbon monoxide and methanol in the presence of a catalyst system comprising a cobalt-containing compound from the group consisting of one or more oxides of cobalt, cobalt salts of a mineral acid, cobalt salts of an organic carboxylic acid and cobalt carbonyl or hydrocarbonyl derivatives, and a promoter selected from the group consisting of: (a) an organo-sulphur compound containing one or more sulphur atoms bonded to one or more carbon atoms from the group consisting of phenylsulphide, diphenyl sulphoxide, dimethylsulphoxide, dibutylsulphide, cis-bis(1,2-benzylthio)ethane, and 1,2-dimercapto-4-methylbenzene, (b) a nitrogen-containing compound, containing one or more tertiary nitrogen donor atoms bonded to one or more carbons atoms in combination with an iodide-containing form of said cobalt-containing compounds and (c) 1,1'-bis(diphenylphosphino)ferrocene, heating said reaction mixture to a temperature of from 50° C. to about 350° C. and at a pressure of 500 psi or greater.

2. The process of claim 1 wherein the cobalt-containing compound is selected from the group consisting of cobalt(II) oxide, cobalt chloride, cobalt(II) iodide, cobalt nitrate, cobalt sulfate, cobalt(II) acetate, cobalt(II) propionate, cobalt(II) acetylacetonate, and dicobalt octacarbonyl.

3. The process of claim 1 wherein the cobalt containing compound is dicobalt octacarbonyl.

4. The process of claim 1 wherein the iodide-containing cobalt compound is cobalt(II) iodide.

5. The process of claim 1 wherein said organo-sulphur compound is selected from the group consisting of diphenylsulphoxide and diphenylsulphide.

6. The process of claim 1 wherein said nitrogen-containing promoter is selected from the group consisting of N-heterocyclic compounds, aliphatic amines and aliphatic nitriles.

7. The process of claim 7 wherein said nitrogen-containing promoters are selected from the group consisting of 8-hydroxyquinoline, 2-hydroxypyridine, N,N,N',N'-tetramethylethylenediamine and succinonitrile.

8. The process of claim 1 wherein said synthesis is conducted in the presence of an inert solvent.

9. The process of claim 8 wherein said inert solvent is an oxygenated hydrocarbon.

10. The process of claim 9 wherein the oxygenated hydrocarbon solvent is selected from the group consisting of 1,3-dioxane, 1,4-dioxane, isopropyl ether, diethylene glycol dibutyl ether, dibutyl ether, ethyl butyl ether and methyl isobutyl ketone.

11. The process of claim 1 wherein the preferred temperature is from about 100° C. to about 250° C.

12. The process of claim 1 wherein the preferred pressure is from about 1,000 psig to about 10,000 psig.

13. The process of claim 1 wherein the cobalt-containing compound is dicobalt octacarbonyl, the promoter is 1,1'-bis(diphenylphosphino)ferrocene and the solvent is p-dioxane.

14. The process of claim 1 wherein the cobalt-containing compound is cobalt(II) iodide, the promoter is 1,1'-bis(diphenylphosphino)ferrocene and the solvent is p-dioxane.

* * * * *